US006406710B1

(12) United States Patent
Panayotatos

(10) Patent No.: US 6,406,710 B1
(45) Date of Patent: Jun. 18, 2002

(54) PROTEIN OCCLUSION FOR DELIVERY OF SMALL MOLECULES

(76) Inventor: Nikos Panayotatos, 95 Monmouth Ct., Orangeburg, NY (US) 10962-2711

( * ) Notice: Subject to any disclaimer, the term of this patent is extended or adjusted under 35 U.S.C. 154(b) by 0 days.

(21) Appl. No.: 09/101,860

(22) PCT Filed: Jan. 16, 1997

(86) PCT No.: PCT/US97/00675

§ 371 (c)(1), (2), (4) Date: Jul. 16, 1998

(87) PCT Pub. No.: WO97/26275

PCT Pub. Date: Jul. 24, 1997

(51) Int. Cl.[7] .......................... A61F 2/02; A61F 13/02; A61K 9/48; A61K 9/20; A61L 9/04

(52) U.S. Cl. ......................... 424/423; 424/45; 424/430; 424/433; 424/434; 424/436; 424/443; 424/451; 424/464

(58) Field of Search ................................ 424/400, 489, 424/490, 101, 45, 423, 430, 433, 434, 436, 443, 451, 464

(56) References Cited

U.S. PATENT DOCUMENTS 4,444,744 A * 4/1984 Goldenberg ................ 424/1.1

OTHER PUBLICATIONS

Arakawa et al. "Formation of heterodimers from three neurotrophins, nerve growth factor, neurotrophin–3, and brain–derived neurotrophic factor" J Biol Chem, 269, pp. 27833–27839 (1994).

Chan et al., "A murine cytokine fusion toxin specifically targeting the murine GM–CSF receptor on normal committed bone marrow progenitor cells and GM–CSF–dependent tumor cells" Blood, 86, pp. 2732–2740 (1995).

Chan et al., "Reactivity of murine cytokine fusion toxin, diphtheria toxin390–murine interleukin–3 (DT390–mIL–3), with bone marrow progenitor cells" Blood, 88, pp. 1445–1446 (1996).

Eriksson et al., "A cavity–containing mutant of T4 lysozyme is stabilized by buried benzene" Nature, 355, pp. 371–373 (1992).

Eriksson et al., "Refined structure of bovine carbonic anhydrase III at 2.0 Å resolution" Proteins, 16, pp. 29–42 (1993).

Eriksson et al., "Similar hydrophobic replacements of Leu99 and Phe153 within the core of T4 lysozyme have different structural and thermodynamic consequences" J. Mol. Biol., 229, pp. 747–769 (1993).

Fulda et al., "Antiproliferative potential of cytostatic drugs on neuroblastoma cell in vitro" European J. Cancer, 31A, 616–21 (1995).

Herrmann et al., "Mediation of NGF–stimulated extracellular matrix invasion by the human melanoma low–affinity p75 neurotrophin receptor: melanoma p75 functions independently of trkA" Mol. Biol. Cell, 4, pp. 1205–1216 (1993).

Kita et al., "Contribution of the surface free energy perturbation to protein–solvent interactions" Biochemistry, 33, pp. 15178–15189 (1994).

Kleywegt et al., Acta Crystallogr., D50, pp. 178–185 (1994).

Matthews et al., "Studies on protein stability with T4 lysozyme" Adv. Protein Chem., 46, pp. 249–278 (1995).

McDonald et al. "New protein fold revealed by a 2.3–Å resolution crystal structure of nerve growth factor" Nature, 354, pp. 411–414 (1991).

Morton et al., "Energetic origins of specificity of ligand binding in an interior nonpolar cavity of T4 lysozyme" Biochemistry, 34, pp. 8564–8575 (1995).

Morton et al., "Specificity of ligand binding in a buried nonpolar cavity of T4 lysozyme: linkage of dynamics and structural plasticity" Biochemistry, 34, pp. 8576–8588 (1995).

Nakagawara et al., "Expression and function of TRK–B and BDNF in human neuroblastomas" Mol. Cell Biol., 14, pp. 759–767 (1994).

Or et al., "Effects of competitive sodium–like antagonists on Na, K–ATPase suggest that cation occlusion from the cytoplasmic surface occurs in two steps" J. Biol. Chem., 268, pp. 16929–16937 (1993).

Panayotatos et al., "Localization of Functional Receptor Epitopes on the Structure of Ciliary Neurotrophic Factor Indicates a Conserved, Function–related Epitope Topography among Helical Cytokines" J. Biol. Chem., 270, pp. 14007–14014 (1995).

Panayotatos et al., "Recombinant human CNTF Receptor a: Production, Binding Stoichiometry and Characterization of Its Activity as a Diffusible Factor" Biochemistry, 33, pp. 5813–5818 (1994).

(List continued on next page.)

*Primary Examiner*—Carlos Azpuru
(74) *Attorney, Agent, or Firm*—Fish & Neave; James F. Haley, Jr.; S. Craig Rochester

(57) ABSTRACT

The present invention relates to complexes between (1) a target-binding moiety; (2) a cavity-forming moiety; and (3) a pharmacological compound to be delivered to a target, wherein the pharmacological compound is buried inside of the cavity-forming moiety, but not covalently bound to either the target-binding moiety or the cavity-forming moiety. The complexes of thus invention may be used as to deliver a pharmacological compound to cells, tissues, organs, viruses, microorganisms or other surfaces that are characterized by an entity that binds the target-binding moiety portion of the complex. The present invention also relates to pharmaceutical compositions comprising the non-covalent complexes of this invention. The invention also relates to methods of delivering a pharmacological compound to a target in a patient. The present invention also relates to the use of the complexes of this invention for the separation of chemical entities from their chiral forms or contaminants.

20 Claims, No Drawings

OTHER PUBLICATIONS

Pedersen et al., "Cavity mutants of Savinase. Crystal structures and differential scanning calorimetry experiments give hints of the function of the buried water molecules in subtilisins" J. Mol. Biol., 242, pp. 193–202 (1994).

Radziejewski C. and Robinson R. C. "Heterodimers of the neurotrophic factors: formation, isolation, and differential stability" Biochemistry, 32, 13350–6 (1993).

Robinson et al., "Structure of the Brain Derived Neurotrophic Factor/Neurotrophia 3 Heterodimer" Biochemistry, 34, pp. 4139–4136 (1995).

Weiner, "The role of growth factor receptors in central nervous system development and neoplasia" Neurosurgery, 37, pp. 179–194 (1995).

* cited by examiner

PROTEIN OCCLUSION FOR DELIVERY OF SMALL MOLECULES

This application is a 371 of PCT/US97/00675 filed Jan. 16, 1997.

TECHNICAL FIELD OF THE INVENTION

The present invention relates to complexes between (1) a target-binding moiety; (2) a cavity-forming moiety; and (3) a pharmacological compound to be delivered to a target, wherein the pharmacological compound is occluded inside of the cavity-forming moiety, but not covalently bound to either the target-binding moiety or the cavity-forming moiety. The complexes of this invention may be used as to deliver a pharmacological compound to cells, tissues, organs, viruses, microorganisms or other surfaces that are characterized by an entity that binds the target-binding moiety portion of the complex. The present invention also relates to pharmaceutical compositions comprising the non-covalent complexes of this invention. The invention also relates to methods of delivering a pharmacological compound to a target in a patient. The present invention also relates to the use of the complexes of this invention for the separation of chemical entities from their chiral forms or contaminants.

BACKGROUND OF THE INVENTION

The formulation and specific delivery of agonists and antagonists to their targets is of fundamental importance in modern pharmacology. Frequently, the pharmacological activity at the target (e.g., cytotoxicity towards malignant tissue in cancer therapy) is complicated by undesired activity at other sites (e.g., cytotoxicity towards healthy tissue).

To improve selective delivery at the molecular level, the specificity of monoclonal antibodies has been exploited for the delivery of antibody/protein fusions to target cells. The use of antibodies as carrier vehicles confers high specificity for the target, but has the disadvantage that release of the protein from the antibody when the fusion reaches the target site is difficult and inefficient. Moreover, antibody/protein fusions often raise neutralizing antibodies which prevent the fusions from reaching its target, thus rendering treatment ineffective. Finally, the type of compound that can be effectively fused to antibodies is mostly limited to larger compounds, such as cytotoxic peptides or proteins. It is extremely difficult to covalently link inorganic or organic molecules to proteins at precise ratios and without loss of protein function.

An alternative method to improve selective delivery at the molecular level is to take advantage of the known specificity of receptor/peptide ligand interactions and make ligand/toxin fusions that selectively destroy cells displaying the cognate receptor. This method also has the disadvantages and limitations of the antibody/toxin fusions. Accordingly, there is a great need for a target-specific delivery system that can overcome these problems, especially one that is useful for the selective delivery of small molecules to desired targets.

Many enzymes contain cavities or channels at their catalytic centers. Such cavities are filled with water molecules that can be exchanged with other solvents (Y. Kita et al., "Contribution of the surface free energy perturbation to protein-solvent interactions" *Biochemistry* 33, pp. 15178–89 (1994)]. Certain enzymes, such as Na,K-ATPase, whose active sites accommodate charged substrates can also occlude small inorganic cations [E. Or et al., "Effects of competitive sodium-like antagonists on Na,K-ATPase suggest that cation occlusion from the cytoplasmic surface occurs in two steps" *J. Biol. Chem.,* 268, pp. 16929–37, (1993)]. Moreover, water filled pockets that appear to be completely buried in the interior of a protein have also been seen in crystal structures of enzymes. The reasons for the existence of empty or water-filled cavities within the tightly packed hydrophobic interior of a protein remain unknown. In the case of a subtilisin, the water was proposed to become trapped as the newly synthesized protein is folded [J. T. Pedersen et al., "Cavity mutants of Savinase. Crystal structures and differential scanning calorimetry experiments give hints of the function of the buried water molecules in subtilisins" *J. Mol. Biol.,* 242, pp. 193–202 (1994)].

The most extensively characterized hydrophobic cavity in the core of an enzyme is that of T4 lysozyme [B. W. Matthews et al., "Studies on protein stability with T4 lysozyme" *Adv. Protein Chem.,* 46, pp. 249–278 (1995)]. The presence of this cavity provided a useful tool for the study of the importance of hydrophobic forces in protein packing. Using directed mutagenesis, Matthews et al. altered the volume of hydrophobic amino acid side-chains protruding into the cavity and, by diffusion, altered the occupancy of the cavity by solvents of increasing hydrophobicity. The consequences of these modifications on the size and shape of the cavity as well as the structure, function and stability of T4 lysozyme were determined by X-ray crystallography, calorimetry and binding measurements (A. E. Eriksson et al., "A cavity-containing mutant of T4 lysozyme is stabilized by buried benzene" *Nature,* 355, pp. 371–3 (1992); A. E. Eriksson et al., "Similar hydrophobic replacements of Leu99 and Phe153 within the core of T4 lysozyme have different structural and thermodynamic consequences" *J. Mol. Biol.* 229, pp. 747–769 (1993); A. Morton et al., "Energetic origins of specificity of ligand binding in an interior nonpolar cavity of T4 lysozyme" *Biochemistry* 34, pp. 8564–75, (1995); A. Morton et al., "Specificity of ligand binding in a buried nonpolar cavity of T4 lysozyme: linkage of dynamics and structural plasticity" *Biochemistry,* 34, pp. 8576–88 (1995)].

Through this work, it became apparent that, within limits, the cavity in the hydrophobic core of T4 lysozyme can be modified or occupied by hydrophobic solvents with little effect on the overall structure of the protein. Such modified cavities could accommodate compounds as large as 161 $Å^3$, with dissociation constants in the 14 to 500 micromolar range—range comparable to many enzyme-substrate binding constants [A. Morton et al. (1995), supra].

The presence of cavities in the hydrophobic cores of non-enzymatic proteins has largely been ignored, since no apparent significance could be ascribed to their presence. For example, the presence of a cavity in the subunit interface of nerve growth factor (NGF) was not reported in a document describing that compound's crystal structure (N. Q. McDonald et al. "New protein fold revealed by a 2.3-Å resolution crystal structure of nerve growth factor" *Nature* 354, pp. 411–14 (1991)]. More recently, however, in a comparison of the structure of a Brain Derived Neurotrophic Factor (BDNF)/Neurotropain-3 (NT-3) heterodimer with that of the NGF homodimer, the preservation of a cavity in both structures was observed. It was postulated that the purpose of that cavity may be to facilitate structural change upon receptor binding [C. R. Robinson et al., "Structure of the Brain Derived Neurotrophic Factor/Neurotrophin 3 Heterodimer" *Biochemistry,* 34, pp. 4139–36 (1995)]. Cavities have also been reported in the structures of other cytokines, such as IL-1 and fibroblast growth factor-β, FGFβ. With the availability of cavity-locating computer programs [G. J. Kleywegt et al., *Acta Crystallogr.,* D50, pp. 178–185 (1994)] and the increasing number of crystal structures being resolved, it is expected that the existence of cavities will be documented in many more proteins. As in the case of the BDNF/NT-3 heterodimer interface, cavities may also be present at the interfaces of other multi-protein complexes, such as the TGF-β covalent dimer and the CNTF/receptor complex or at complexes of proteins with other macromolecules, such as a fibroblast growth factor (FGF)/heparin complex.

SUMMARY OF THE INVENTION

The present invention solves the problems set forth above by providing complexes between (1) a target-binding moiety; (2) a cavity-forming moiety; and (3) a pharmacological compound to be delivered to a target, wherein the pharmacological compound is occluded inside of the cavity-forming moiety, but is not covalently bound to either the cavity-forming moiety or the target-binding moiety. The complexes of this invention are able to deliver the pharmacological compound to a desired location in a patient through the specificity of the target-binding moiety for the target. At the same time, the cavity-forming moiety in the complexes of the invention traps the pharmacological compound until it reaches the target. This serves the dual purpose of protecting the pharmacological compound from degradation or clearance before it reaches the desired target, as well as specifically directing the pharmacological compound to the target. This latter feature is useful in preventing unwanted side effects that may be caused by having the pharmacological compound interact with non-target cells. Once the complex reaches and interacts with the target through its target-binding moiety, the pharmacological compound is released due to an unfolding or internalization of the complex triggered by the target-complex interaction.

The invention also provides pharmaceutical compositions comprising the complexes of this invention and a pharmaceutically acceptable carrier. These compositions are useful in methods for treating various diseases in which it is necessary to deliver a pharmacological compound to a specific target. Such methods are also part of the present invention.

Finally, the invention provides methods which utilize the complexes of this invention to separate desired compounds from their unwanted chiral forms and other contaminants.

DETAILED DESCRIPTION OF THE INVENTION

According to one embodiment, the invention provides complexes between (1) a target-binding moiety; (2) a cavity-forming moiety; and (3) a pharmacological compound to be delivered to a target, wherein the pharmacological compound is occluded inside of the cavity-forming moiety, but is not covalently bound to either the cavity-forming moiety or the target-binding moiety.

The target binding moiety of the complexes of this invention may be any moiety that can bind a target (e.g., a molecule, cell, virus, bacteria) or can be internalized by the target. Of course, the target-binding moiety must also be capable of maintaining its ability to bind the target when it is part of the complex of this invention. Thus, the target-binding moiety may be a protein or a portion of a protein, glycoprotein or lipid-modified protein. These include antibodies, such as a monoclonal, polyclonal antibody or the $F_{ab}$ region of an antibody; peptidic ligands, such as CD4 binding proteins, cytokines, chemokines, neurotrophins, and other tropic and trophic actors that interact with specific receptors, such as cell surface receptors. Alternatively, the target-binding moiety may be non-peptidic, such as a lectin, a polysaccharide, heparin, or other molecules that are specifically bound by a receptor at the target surface or are internalized by the target. The choice of target-binding moiety will, of course, depend upon the nature of the desired target.

The target-binding moiety may be a naturally occurring moiety or may be synthetically produced, either by recombinant DNA techniques, peptide synthesis techniques, organic synthesis techniques, or combinations of the above, depending upon the nature of the moiety. Preferred target-binding moieties useful in the complexes of this invention are the NGF-family of neurotrophic factors, their chimeras, IL-1, IL-2, IL-3 and other interleukins, GM-CSF, EGF, FGF, TGFb and IgG.

The cavity-forming moiety in the complexes of this invention is any moiety that is capable of forming pockets of sufficient size to carry the pharmacological compound component of the complex. These pockets are preferably present in the cavity-forming moiety even when it is not complexed with the pharmacological compound. Thus, the cavity may be a natural site of a protein or a site created or modified by substituting side chains of specific amino acids that make up the cavity by means of genetic engineering. Alternatively, the cavity may be a site that is only created when the cavity-forming moiety is complexed with the pharmacological compound. Preferably, the cavity-forming moiety is a protein or a complex of proteins such as Na,K-ATPase, the BDNF/NT-3 heterodimer, the NGF dimer, IL-1 and FGFβ. Preferred cavity-forming moieties useful in the complexes of this invention are the NGF-family of neurotrophic factors, their chimeras, IL-1b, IL-2, IL-3 and other interleukins, GM-CSF, EGF, FGF, barnase, T4 lysozyme, TGFb and IgG.

The target-binding moiety and the cavity forming moiety must be bound to one another in such a way so as to maintain the integrity of the resulting complex. According to a preferred embodiment, the target binding moiety and cavity-forming moiety are part of the same molecule, such as a fusion protein or a target-binding protein that has sufficient three-dimensional structure to form a cavity. Alternatively, these two moieties may be conjugated to one another through the use of cross-linking reagents or other well-known conjugation methods. It is also possible, however, that these two moieties bind specifically to one another, as for example in the complexes of CNTF and IL-6 with their soluble receptors.

The third component of the complexes of this invention is the pharmacological compound. This compound may be any molecule that exerts its action at the target, causing activation or inhibition of biological activity or other pharmacological action. The choice of pharmacological compound will depend on the intended use of the complex (e.g., the disease state to be treated), the nature of the target (e.g., cells, virus, bacteria, etc.), the ability of the complex to effectively carry that compound (e.g., the size of the pockets formed by the cavity-forming moiety), and the compatibility of that compound with the other moieties of the complex in terms of not obliterating the ability of the complex to bind the target. Preferably, the pharmacological compound is smaller than 800 $Å^3$ and more preferably smaller than 400 $Å^3$.

It is also preferred that the pharmacological compound bind to the complex (and in particular, the cavity-forming moiety) with a dissociation constant of less than 1.0 mM, and even more preferably, less than 0.1 mM.

Examples of pharmacological compounds that may be used in the complexes of this invention are ions; such as $Ca^{2+}$ and $Zn^{++}$; radioisotopes used in diagnosis and therapy, such as $^{99m}$Tc, $^{67}$Cu, and $^{90}$y; small compounds, such as urea, phenol and salicylic acid derivatives; cytotoxic drugs, such as cis-platinum, nitrosourea, etoposide, vincristine, lysodren, ifosfamide, myleran, thiotepa and other nitrogen mustard derivatives, hydroxyurea, carmustine, other nitrosourea derivatives; antiviral drugs, such as AZT, 3TC, Cidofovir and HIV protease inhibitors; antibiotics; and prodrugs that are converted to active forms after uptake by the target tissue.

The complexes of this invention may be formed by simply dispersing an at least 10-fold, and more preferably an at least 100-fold, molar excess of the pharmacological compound in a solution and then adding to that solution the cavity-forming moiety, either alone or together with the target-binding moiety if those two moieties are part of the same molecule. Depending on the nature of the cavity-forming moiety and the pharmacological compound, occlusion of the pharmacological compound within the cavity-forming moiety may be facilitated by unfolding and refolding the cavity-forming moiety in the presence of the compound. Unfolding of the cavity-forming moiety may be achieved by standard techniques known in the art, including altering the pH of the solution for a brief period of time, raising the temperature for a brief period of time, increasing salt concentration, or adding a mild denaturant, such as urea or guanidine. In some situations, the pharmacological compound itself will unfold the cavity-forming domain, such as when it is a denaturant itself or an organic solvent.

Refolding is also achieved by standard techniques which remove the denaturant or return the solution to its original state, such as by dialysis, acid or base addition, cooling, removing the excess pharmacological compounds, etc.

The target-binding moiety, if not already added to the complex as part of a molecule containing the cavity-forming moiety, may then be non-covalently bound or chemically conjugated to the cavity-forming moiety/pharmacological compound complex through standard techniques.

The target-binding moiety in the complex must of course retain its ability to bind the target with specificity. The complex, however, need not display the biological activity or conformation of either the target-binding moiety or the cavity-forming moiety, as long as it retains sufficient binding preference for the target. In certain instances, the lack of biological activity of these two moieties may be preferable.

The target for the complexes of this invention may be any entity that is capable of binding the target-binding moiety of the complexes of this invention and to which one wants to deliver the pharmacological compound in the complex. Thus, targets include molecules, cells, tissues, organs, viruses, bacteria, fungi or any other surface that displays an affinity for the target-binding moiety. Examples of preferred targets are cells that express surface receptors, proteins and other ligand-binding components, such as the cytokine and neurotrophin receptors, CD4 and various cell, microbial and viral antigens.

Release of the pharmacological compound at the target is effected by the events following the binding of the target-binding moeity to the target. These include passive diffusion of the pharmacological compound out of the complex, proteolysis of the complex, the conformationas changes of the complex following its binding to the target or binding to the target followed by internalization and protein degradation.

The specificity and affinity of the complex for its target can be determined by any of several established procedures, such as those relating to the binding of protein ligands to their cognate receptors or those measuring biological activity, e.g. Panayotatos, N., Everdeen, D., Liten, A., Somogyi, R. and Acheson, A. "Recombinant human CNTF Receptor a: Production, Binding Stoichiometry and Characterization of Its Activity as a Diffusible Factor" *Biochemistry,* 33, 5813–5818 (1994).

The molar ratio of occluded ligand(s) per molecule of protein, will be determined by mass spectrophotometric and other established analytical techniques. Such techniques could be applied directly to the complex or to its components after separation by reversed phase, or other chromatographic technique.

In cases where the compound occluded in the complex has established pharmacological activity, the therapeutic dose of the compound will guide the dose of the complex to be used in therapy. As a starting point, the complex will be administered alone at a therapeutic dose equimolar to the therapeutic dose of the compound alone. Alternatively, the complex will be co-administered with the compound, each at one half the molar therapeutic dose of the compound alone. The efficacy of the complex relative to the compound will also be assessed from in vitro assays using primary cells and cell lines.

Routes of administration will naturally vary with the pathological condition. In cases where the compound occluded in the complex has an established route of administration, the same route may be followed.

The present invention also relates to pharmaceutical compositions comprising the complexes of this invention and a pharmaceutically acceptable carrier. Pharmaceutical compositions of this invention comprise any of the complexes of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, polyethyleneglycol polymers such as PEG-400, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solublized derivatives may also be advantageously used to enhance delivery of the complexes of this invention.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles.

In some cases, the pH of the formulation may be adjusted with pharmaceutically acceptable acids, bases or buffers to enhance the stability of the formulated complex or its delivery form. The term parenteral as used herein includes subcutaneous, intracutaneous, intravenous, intramuscular, intra-articular, intrasynovial, intrasternal, intrathecal, intralesional, and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as carboxymethyl cellulose or similar dispersing agents which are commonly used in the formulation of pharmaceutically acceptable dosage forms such as emulsions and or suspensions. Other commonly used surfactants such as Tweens and Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, hard or soft gelatin capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the complex may be suspended or dissolved in an oily phase combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a complex of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the complex suspended or dissolved in a carrier with suitable emulsifying agents. Carriers for topical administration of the complexes of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active complex suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active complex are useful in the delivery of pharmacological compounds to a target in a patient. Typically, the pharmaceutical compositions of this invention will be administered from about 1 to about 5 times per day or alternatively, as a continuous infusion. Such administration can be used as a chronic or acute therapy. The amount of complex that may be combined with the carrier materials to produce a single dosage form will vary depending upon the host treated and the particular mode of administration. A typical preparation will contain from about 5% to about 95% active complex (w/w). Preferably, such preparations contain from about 20% to about 80% active complex.

Upon improvement of a patient's condition, a maintenance dose of a complex, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific complex employed, the age, body weight, general health status, sex, diet, time of administration, rate of excretion, drug combination, the severity and course of the infection, the patient's disposition to the infection and the judgment of the treating physician.

According to another embodiment, the present invention provides a method of delivering a pharmacological compound to a target. This method is especially useful in treating diseases with compounds that can cause adverse side effects in non-target cells, tissues and organs, such as in the delivery of toxic compounds to cancer cells, viruses or bacteria.

Preferably, the target contains a protein that binds to the complex. Even more preferably, that protein is a receptor. More preferred targets are those that contain a cytokine receptor, a chemokine receptor, a seven-pass transmembrane receptor, a neurotrophin receptor or a cell surface antigen on their surface. Most preferred targets are those that express trkA, trkB, trkC, p75, IL-1R, IL-2Ra, IL-3R, GM-CSFR, EGFR, FGFR, CD33 or CD4 on their surface.

The beauty of the methods of this invention is that at a given dose, more compound will reach the target tissue relative to the non-target tissue because the compound is preferably delivered to the target. Thus, these methods achieve higher concentrations of compound at the desired site without the concomitant high serum level of compound that is inherent in standard delivery systems (e.g., parenteral injection or other administration of the compound alone) and is responsible for undesirable dose-limiting side effects.

According to yet another embodiment, the invention provides methods of separating a compound from its chiral forms and other contaminants. Such methods comprise combining mixtures of pharmacological compounds with target-binding and cavity-forming moieties. The resulting complex, containing the desired occluded compound, is then separated from the the unwanted chiral forms and other contaminants. The complex is then treated such that the desired compound is released from the the complex.

In order that this invention be more fully understood, the following examples are set forth. These examples are for the purpose of illustration only and are not to be construed as limiting the scope of the invention in any way.

EXAMPLES

Many applications of the complexes of this invention in therapy will be similar to those applications where immunotoxin therapy is used. In both situations, the therapeutic agent comprises a binding moiety and a toxin, and the guiding principle is to improve the delivery of the toxin to the target relative to non-target tissue. Therefore, the pathophysiological conditions treatable with immunotoxins will also be amenable to treatment with complexes of this invention. Immunotoxin applications are based on the observation that certain cell surface proteins are expressed, or even overexpressed, in malignant relative to normal cells. Among these proteins are several cytokine receptors, and relevant immunotoxins consist of the cognate protein ligand fused or covalently linked to a toxin. Examples of malignant cell-specific receptors include the EGFR in squamous carcinoma, adenocarcinoma and melanoma, the FGFR in breast cancer and glioblastoma, the IL-3R in myeloid leukemia, the GM-CSFR in acute myeloid leukemia and the NGF-like neurotrophin receptors in neuroblastoma (H. L. Weiner, "The role of growth factor receptors in central nervous system development and neoplasia" *Neurosurgery,* 37, pp. 179–94 (1995); C. H. Chan et al., "Reactivity of murine cytokine fusion toxin, diphtheria toxin390-murine interleukin-3 (DT390mIL-3), with bone marrow progenitor cells" *Blood,* 88, pp. 1445–46 (1996); C. H. Chan et al., "A murine cytokine fusion toxin specifically targeting the murine GM-CSF receptor on normal committed bone marrow progenitor cells and GM-CSF-dependent tumor cells" *Blood,* 86, pp. 2732–40 (1995).

It will be apparent to those of skill in the art to seek such examples of immunotoxin applications when determining the choice of components for the complexes of the present invention. Some of these are set forth below by way of example.

Example 1

Occlusion of Chemotherapeutic Compounds into the Cavity of a Protein Ligand of a Receptor that is Expressed in Malignant Cells for Use in Therapy A first example of practicing this invention is the occlusion of a compound into the cavities formed at the dimer interface of NGF. To practice the invention those of skill in the art would pursue the following steps:

a) Identify in the medical literature a malignant condition, in this example a neuroblastoma.

b) Identify in the medical literature a target that is expressed (preferably overexpressed) in said condition, in this case the trkA receptor.

c) Identify in the medical literature a protein ligand of known, structure for that receptor, in this case NGF.

d) Identify buried water molecules or a cavity in the structure of NGF (see, N. Q. McDonald et al. "New protein fold revealed by a 2.3-Å resolution crystal structure of nerve growth factor" *Nature* 354, pp. 411–14 (1991)) and determine the size of the cavity, as described by Kleywegt G. J., Jones, T. A. *Acta Crystallogr, D*50, 178–185, 1994.

e) If the cavity is sufficiently large (preferably greater than 30 $Å^3$), proceed with testing as in (h) below.

f) Enlarge the cavity if it is not sufficiently large or does not have the desired shape or hydrophobicity features, using the approaches of B. W. Matthews, "Studies on protein stability with T4 lysozyme" *Advances in Protein Chemistry,* 46, pp. 249– 278 (1995); and A. E. Eriksson et al., "A cavity-containing mutant of T4 lysozyme is stabilized by buried benzene" *Nature,* 355, pp. 371–3 (1992). As described therein, the dimensions of a cavity and the polarity of its environment can be altered and studied by means of genetic engineering aided by information from X-ray structures and computer models. Such methodology was used to alter the cavity of T4 lysozyme in order to study the importance of the hydrophobic effect on protein packing [A. E. Eriksson et al., "Similar hydrophobic replacements of Leu99 and Phe153 within the core of T4 lysozyme have different structural and thermodynamic consequences" *J. Mol. Biol.* 229, 747–769 (1993); A. E. Eriksson et al., "Refined structure of bovine carbonic anhydrase III at 2.0 Å resolution" *Proteins,* 16, pp. 29–42 (1993); the disclosures of each of which is herein incorporated by reference].

Similar methodology can be used to create a cavity that can accommodate specific compounds of known structure and variable polarity in NGF or other proteins.

It will be appreciated by those of skill the art that known methods of protein engineering such as those described by N. Panayotatos et al., "Localization of Functional Receptor Epitopes on the Structure of Ciliary Neurotrophic Factor Indicates a Conserved, Function-related Epitope Topography among Helical Cytokines" *J. Biol. Chem.,* 270, pp. 14007–14 (1995), the disclosure of which is herein incorporated by reference, can be used to delete, replace or add amino acid residues to a recombinant protein in order to create a cavity.

g) Identify in the medical literature, such as the Physician's Desk Reference, a list of antineoplastic drugs. Limit the number of compounds to be tested to those with molecular weight less than 1,000, as a first approximation of molecules having a volume less than 800 $Å^3$.

h) Test for passive occlusion into the cavity of NGF using the method of A. Morton et al., "Energetic origins of specificity of ligand binding in an interior nonpolar cavity of T4 lysozyme" *Biochemistry,* 34, pp. 8564–75 (1995), whereby the protein (1 mM final concentration) is added to a solution of the compound at 0.1 mM final concentration in near-physiological buffer. Test three control compounds, ethylbenzene, benzofuran and isobutylbenzene, and the selected antineoplastic drugs. If desirable, determine dissociation constants for each occluded compound as described in the above article. Select compounds with dissociation constants less than 1 mM.

i) Active occlusion. If the passive occlusion tests above do not reveal occlusion of the desired compounds or if the affinity of the occluded compounds are not sufficiently high, facilitate occlusion using one of the following methods.

1) Denature and renature the mixture of carrier plus compound by brief exposure to moderate heat, preferably in the range 40° C.–90° C. Return the solution to room or lower temperature and test for occlusion.

2) Denature and renature the mixture of carrier plus compound by brief exposure to non-neutral pH, preferably in the range 1–5 and 9–14. Return the solution to neutral pH and test for occlusion.

3) Expose the mixture of carrier plus compound to a high ionic strength (e.g. high concentration of NaCl). Remove the salt (e.g. by dialysis) in the presence of a large excess of the compound and test for occlusion.

4) Expose the mixture of carrier plus compound to a denaturant, such as urea or guanidine. Remove the denaturant (e.g. by dialysis) in the presence of a large excess of the compound and test for occlusion.

5) Expose the carrier to a high concentration of the compound (depending on its chemical nature the compound, may also serve as the denaturant). Remove the excess of compound (e.g. by dialysis) and test for occlusion.

It will be appreciated by those of skill in the art that other methods of recombinant protein refolding can be used to facilitate occlusion. In the specific example of NGF, reversible dissociation and reassociation of the subunits of the dimeric carrier protein can be effected as described by Radziejewski C. and Robinson R. C. "Heterodimers of the neurotrophic factors: formation, isolation, and differential stability" *C. Biochemistry* 32: 13350–6 (1993) or by Arakawa, T. et al. "Formation of heterodimers from three neurotrophins, nerve growth factor, neurotrophin-3, and brain-derived neurotrophic factor" *J. Biol. Chem.* 269 27833–9 (1994).

j) Identify in the medical literature a neuroblastoma cell line that expresses the trkA receptor, e.g. SMS-KCN cells (A. Nakagawara et al., "Expression and function of TRK-B and BDNF in human neuroblastomas" *Mol. Cell. Biol.,* 14, pp. 759–67 (1994).

k) Identify in the medical literature a method for testing the toxicity of drugs on neuroblastoma cells, such as the method of S. Fulda et al., "Antiproliferative potential of cytostatic drugs on neuroblastoma cells in vitro" *Eur. J. Cancer,* 31A, pp. 616–21 (1995). The ED50 values for 16 out of 20 cytostatic drugs tested with this method were found to fall in the 0.02–10 $\mu$M range, comparable to peak serum levels achieved in patients during chemotherapy. Therefore, this method can be used to test occluded compounds directly at clinically relevant concentrations.

l) Using said method, determine the ED50 of drugs that were identified as capable of occlusion in NGF.

m) Using said method, determine the ED50of said drugs occluded in NGF. For any occluded compound an ED50 more than twofold lower than the free compound would indicate that occlusion can improve the efficacy of the cytotoxic drug.

n) As a control, identify a cell line that does not express trkA [e.g., MeWo; J. L. Herrmann et al., "Mediation of NGF-stimulated extracellular matrix invasion by the human melanoma low- affinity p75 neurotrophin receptor: melanoma p75 functions independently of trkA" *Mol. Biol. Cell,* 4, pp. 1205–16 (1993)] and repeat the cytotoxicity experiments with free and NGF-occluded drug. The ED50 should be the same within experimental error, indicating that NGF-occlusion preferably directs the cytotoxic drug only to cells that display trkA on their surface, i.e., the desired target tissue.

Example 2

Conversion of Small Molecules into Selective Cytostatic Agents by Occlusion into the Cavity of a Protein Ligand of a Receptor that is Expressed in Malignant Cells Occlusion into the cavity of NGF directs a compound preferably to cells expressing the trkA receptor. In Example 1 the occluded compound is a cytostatic drug. A second way to practice the invention, however, is by occluding compounds from a large library of small molecules that are not necessarily cytostatic. Subsequently, occluded compounds are tested for cytostatic activity.

In this approach, the steps of Example 1 are followed with the exception of step (i). At said step, pools of small compounds (10–100 per pool) are tested for occlusion instead of individual drugs. Subsequently, occluded compounds are separated from the protein in the complex and identified by standard analytical chemistry methodology. The occluded compounds are tested for cytostatic activity, as described in steps (j) through (n) of Example 1.

By this approach, compounds that are not known cytostatic drugs or have very weak cytostatic activity can be rendered effective and selective cytostatic agents.

Example 3

Use of Protein Occlusion for the Separation of Chemical Entities from Their Chiral Forms or Contaminants A third example of practicing the invention is the purification of desired compounds from chiral forms or other contaminants.

One or more compounds are occluded into a carrier protein. Because of the shape and hydrophobicity of the cavity, chiral forms or other contaminants will not be occluded. The complex is separated from free compound by chromatographic techniques, such as gel permeation. Subsequently, the occluded compound is liberated by denaturation of the protein and separated from free protein by the same chromatographic technique.

Alternatively, the carrier protein is immobilized on a suitable surface, such as liquid chromatography beads. The compound is passed through under conditions that will occlude the desired compound. Because of the shape and hydrophobicity of the cavity, chiral forms or other contaminants will not be occluded. Subsequently, the occluded compound will be liberated by reversible denaturation of the protein and eluted from the immobilized protein.

Example 4

Other Uses of the Complexes of this Invention

It will be obvious to those of skill in the art that the compositions and methods disclosed above by way of example are applicable to many carrier proteins other than NGF. For example, the cavity in the BDNF/NT-3 heterodimer interface contains 12 ordered water molecules and is closed, whereas the cavity in NGF has a channel to the exterior of the protein [C. R. Robinson et al., "Structure of the Brain Derived Neurotrophic Factor/Neurotrophin 3 Heterodimer" *Biochemistry,* 34, pp. 4139–4136 (1995)]. Because of this difference in shape and in the amino acid side chains that form each of these cavities, each cavity will accommodate a different variety of compounds with variable affinities. Furthermore, the target for the BDNF/NT-3 heterodimer is the trkB receptor which is expressed in different tissues than trkA and also expressed by certain neuroblastoma cells. Due to the sequence conservation among the four known neurotrophins, other combinations of neurotrophin dimers will be found to contain cavities and be used as carriers.

The invention will also be applicable to proteins without known cavities. In the absence of cavities, water molecules buried in hydrophobic pockets can be identified by computer search of crystal structures and subsequently engineered into cavities of desired size, shape and hydrophobicity, as disclosed above.

An important factor in the choice of carriers will be the pharmacological tolerability of the protein. High tolerability will allow a broader dose range of the occluded compound to be tested. In this respect, BDNF will be of particular interest because it has been found to be well tolerated with insignificant adverse effects at relatively high doses in human clinical trials.

It will also be obvious to those of skill in the art that the compositions and methods disclosed above by way of example are applicable to many targets other than the trkA receptor and other compounds than the cytostatic drugs. By following the approach disclosed in the above examples, different targets can be identified that will be relevant to therapeutic areas other than cancer.

Also, applications other than in vivo therapy will be appreciated, such as ex vivo treatment of bone marrow cells to deplete them of malignant cells before reengraftment. For effective therapy, depletion of malignant cells must be complete but, at the same time, healthy cells must be protected. A major limitation of conventional treatments is that cytotoxic drugs do not discriminate between malignant and healthy cells. By occlusion into an appropriate protein carrier, the cytostatic agent will be delivered to the malignant cells with preference over normal cells, and thus greatly improve the therapeutic index of the drug.

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

I claim:

1. A complex comprising:

a. a target-binding moiety, which in said complex is capable of specifically binding a target;

b. a cavity-forming moiety; and c. a pharmacological compound, wherein:

said pharmacological compound is present in the cavities of said cavity-forming moiety and is bound non-covalently thereto; and said target-binding moiety is bound to said cavity-forming moiety.

2. The complex according to claim 1, wherein said cavity-forming moiety is a recombinant protein.

3. The complex according to claim 1, wherein said target-binding moiety is a recombinant polypeptide.

4. The complex according to any one of claims 1 to 3, wherein said cavity-forming moiety and said target binding moiety are part of a single polypeptide.

5. The complex according to any one of claims 1 to 4, wherein said target-binding moiety comprises a ligand for a cell surface receptor.

6. The complex according to any one of claims 1 to 4, wherein said target-binding moiety comprises an antigen-binding fragment of an antibody.

7. The complex according to claim 6, wherein said antigen-binding fragment binds a cell surface protein.

8. the complex according to any one of claims 1–7, wherein said cavity-forming moiety and said target-binding moiety are each independently a protein selected from the group consisting of the NGF-family of neurotrophic factors, heterodimeric chimeras of neurotrophic factor subunits, interleukins, GM-CSF, EGF, FGF, barnase, T4 lysozyme, TGFb and IgG.

9. The complex according to any one of claims 1–8, wherein said pharmacological compound is bound to said complex with a dissociation constant of less than 1 mM under physiological conditions.

10. The complex according to claim 9, wherein said pharmacological compound is bound to said complex with a dissociation constant of less than 0.1 mM under physiological conditions.

11. The complex according to any one of claims 1–10, wherein said pharmacological compound has a size of less than 800 $Å^3$.

12. The complex according to claim 11, wherein said pharmacological compound has a size of less than 400 $Å^3$.

13. The complex according to any one of claims 1–10, wherein said pharmacological compound is selected from a cytotoxic compound, an antiviral compound, an anti-inflammatory compound, an immunosuppressant, a chemotherapeutic agent, a radioisotope, or an ion.

14. The complex according to claim 13, wherein said pharmacological compound is selected from $Ca^{++}$, $Zn^{++}$, $^{99m}Tc$, $^{67}Cu$, $^{90}Y$, urea, phenol, salicylic acid derivatives, cis-platinum, etoposide, vincristine, lysodren, ifosfamide, myleran, nitrogen mustard derivatives, hydroxyurea, nitrosourea derivatives, antibiotics, AZT, 3TC, Cidofovir, or an HIV protease inhibitor.

15. A pharmaceutical composition comprising a. a complex according to any one of claims 1 to 14 in an amount sufficient to deliver a therapeutic amount of the pharmacological compound present in said complex to a desired target in a patient; and b. a pharmaceutically acceptable carrier.

16. A pharmaceutical composition comprising a. a complex according to any one of claims 1 to 14; and b. a pharmaceutically acceptable carrier.

17. The complex according to any one of claims 1–7, wherein said cavity-forming moiety and said target-binding moiety are selected from the group consisting of IL-1b, IL-2 and IL-3.

18. The complex according to claim 13, wherein said pharmacological compound is thiotepa.

19. The complex according to claim 13, wherein said pharmacological compound is carmustine.

20. The complex according to any one of claims 1–7, wherein more than one pharmacological compound is present in the cavities of the cavity-forming moiety.

* * * * *